(12) United States Patent
Benco et al.

(10) Patent No.: US 6,355,158 B1
(45) Date of Patent: Mar. 12, 2002

(54) METHOD OF MEASURING PH

(75) Inventors: John S. Benco, Holliston; Jan S. Krouwer, Sherborn, both of MA (US)

(73) Assignee: Bayer Corporation, East Walpole, MA (US)

(*) Notice: Subject to any disclaimer, the term of this patent is extended or adjusted under 35 U.S.C. 154(b) by 0 days.

(21) Appl. No.: 09/479,739

(22) Filed: Jan. 7, 2000

Related U.S. Application Data

(60) Provisional application No. 60/115,039, filed on Jan. 7, 1999.

(51) Int. Cl.[7] .................. G01N 27/31; G01N 27/416
(52) U.S. Cl. ................. 205/787.5; 205/792; 205/793; 204/418; 204/433
(58) Field of Search ............... 205/787.5, 792, 205/793; 204/416, 418, 433

(56) References Cited

U.S. PATENT DOCUMENTS

| | | | |
|---|---|---|---|
| 4,511,660 A | * 4/1985 | Lubbers et al. | ............. 204/433 |
| 4,818,361 A | 4/1989 | Burgess et al. | |
| 5,132,000 A | * 7/1992 | Sone et al. | ................. 204/416 |
| 5,554,272 A | 9/1996 | Benco et al. | ............ 205/782.5 |
| 5,595,646 A | 1/1997 | Foos et al. | |

FOREIGN PATENT DOCUMENTS

| | | | |
|---|---|---|---|
| DE | 4025426 | 2/1992 | .......... G01N/33/68 |
| EP | 0362032 | 4/1990 | .......... G01N/33/96 |
| EP | 0364948 | 4/1990 | .......... G01N/27/416 |
| WO | 93/13411 | 7/1993 | .......... G01N/27/26 |
| WO | 98/38503 | 9/1998 | .......... G01N/27/333 |

OTHER PUBLICATIONS

Funck et al, Analytical Chemistry, vol. 54, pp. 423–429, 1982.*

Oesch, U. et al., "Ion–Selective Membrane Electrodes for Clinical Use" *Clin. Chem.* 32/8, pp. 1448–1459 (1986). Month unknown.

* cited by examiner

*Primary Examiner*—Robert J. Warden, Sr.
*Assistant Examiner*—Kaj K. Olsen
(74) *Attorney, Agent, or Firm*—Louis L. Wu; Reed & Associates

(57) ABSTRACT

The present invention provides a means to substantially decrease the pH bias that is commonly observed with pH data obtained using ion selective electrode (ISE) containing instruments that have a solvent polymeric membrane based ISE pH electrode. The pH bias is reduced by utilizing the discovery that the presence of protein in a liquid sample induces an apparent interference with the pH value.

20 Claims, 3 Drawing Sheets

METHOD OF MEASURING PH

This application claims the benefit of U.S. Provisional Application 60/115,039, filed Jan. 7, 1999.

FIELD OF THE INVENTION

This invention relates to non-glass ion selective electrode systems used in the measurement of pH.

BACKGROUND

Electrochemical means for measuring the pH levels of liquid systems are well known. Glass sensors having membrane type of electrodes are commonly used as standards for pH measurements because sensing instruments with glass sensors are widely available commercially and the measurements from the glass sensors are predictable and provide good measuring capability. Glass sensors are fabricated as three-dimensional articles, with many serviceable parts. While demonstrating good measuring capability, these three-dimensional articles are more expensive and complex to manufacture as well as operate as compared to planar format sensors.

Non-glass based pH sensors have also been described in the literature. The non-glass sensors are typically prepared using solvent polymeric membranes (such as those described in *Analytical Chemistry*, 1986, 58, 2285–2289, hereby incorporated by reference). Within the category of non-glass sensors are those of a planar format which is typically smaller than glass sensors and much less expensive to manufacture as well as operate. Examples of planar sensors can be found in U.S. Pat. Nos. 5,554,272; 5,702,575; and 5,786,830, each of which is hereby incorporated by reference. Instruments containing planar sensors are available commercially. The planar format of the sensors typically comprises relatively thin layers of materials which are applied to substrate bases using thick-film or thin-film techniques, including, for example, silk-screen printing.

Non-glass sensors for the measurement of pH offer an economical alternative to glass sensors, but the membrane-based pH sensors have been associated with a scatter of results commonly referred to as pH bias. As used herein, pH bias is defined as equal to measured pH using a membrane based sensor minus measured pH using a known standard which is typically a measurement obtained from a glass based pH sensor. If the pH bias is too great, the error has a potential to approach clinical decision levels. Accordingly, a method of decreasing the pH bias associated with membrane based sensors is needed.

SUMMARY OF INVENTION

The present invention provides a means to substantially decrease the pH bias that is commonly observed with pH data obtained using instruments that have a solvent polymeric membrane based pH electrode. The pH bias is reduced by utilizing the discovery that the presence of protein in a liquid sample induces an apparent interference with the pH value. According to the invention, provided is a method of measuring pH in an ion selective electrode based sensing instrument that employs a polymeric membrane based pH electrode, said method comprising measuring the pH of a protein containing liquid sample using said pH electrode to obtain a raw pH measurement and correcting said raw pH measurement for interference induced by the presence of protein in said liquid sample.

Also provided is a method of reducing the pH bias demonstrated by a planar polymeric membrane based pH ion selective electrode, said method comprising (a) measuring the pH of a protein containing liquid sample using said pH electrode to obtain a raw pH value, (b) obtaining a bicarbonate value of said sample either directly or indirectly, (c) obtaining a corrected pH value by inserting the raw pH value and bicarbonate value into an Equation [1*]

$$\{\text{Corrected pH} = \text{Raw pH} - (a^*[HCO_3^-]^2 + b^*[HCO_3^-] - c)\} \quad [1^*],$$

wherein $a^*$, $b^*$ and $c$ are empirically derived coefficients and $[HCO_3^-]$ represents said bicarbonate value.

Also provided is a method of measuring pH using an ion selective polymeric membrane based electrode, said method comprising (a) contacting a protein containing liquid sample with a polymeric membrane based ion selective electrode specific to pH; (b) contacting said liquid sample with an electrode to derive a bicarbonate value; (c) contacting said liquid sample with at least one reference electrode either directly or indirectly; (d) connecting said exposed contact area of sensor with a sensing instrument; (e) providing an electrical current from said sensing instrument through said reference electrode to derive a raw pH value; (f) correcting said raw pH value by utilizing in said sensing instrument the Equation [1*]

$$\text{Corrected pH} = \text{Raw pH} - (a^*[HCO_3^-]^2 + b^*[HCO_3^-] - c) \quad [1^*]$$

wherein $a^*$, $b^*$ and $c$ are empirically derived coefficients and $[HCO_3^-]$ represents said bicarbonate value.

Also provided is a method of correcting for the presence of protein in liquid samples when using a system comprising a planar polymeric membrane pH ISE electrode, said method comprising using a $[HCO_3^-]$ value measured from said liquid sample in a sensing instrument by inserting a correcting equation into the software of said instrument wherein said equation utilizes the raw pH obtained from said pH ISE electrode and the $[HCO_3^-]$ value. Preferably the pH bias (as verified using a pool of 200 samples run on said instrument and using a three dimensional glass sensor as the standard) is reduced to a level of less than ±0.04 pH units, more preferably equal to or less than ±0.02 pH units.

The invention provides an improvement for any system utilizing solvent polymeric membrane based ion selective electrodes where pH is included as one of the analytes of interest. By incorporating a correction equation into the ion selective electrode based system, pH bias may be substantially lessened. The correction equation may be easily incorporated into the software used in electrode systems that include a membrane based pH electrode by techniques well known to those skilled in the art.

DETAILED DESCRIPTION

Figure 1:
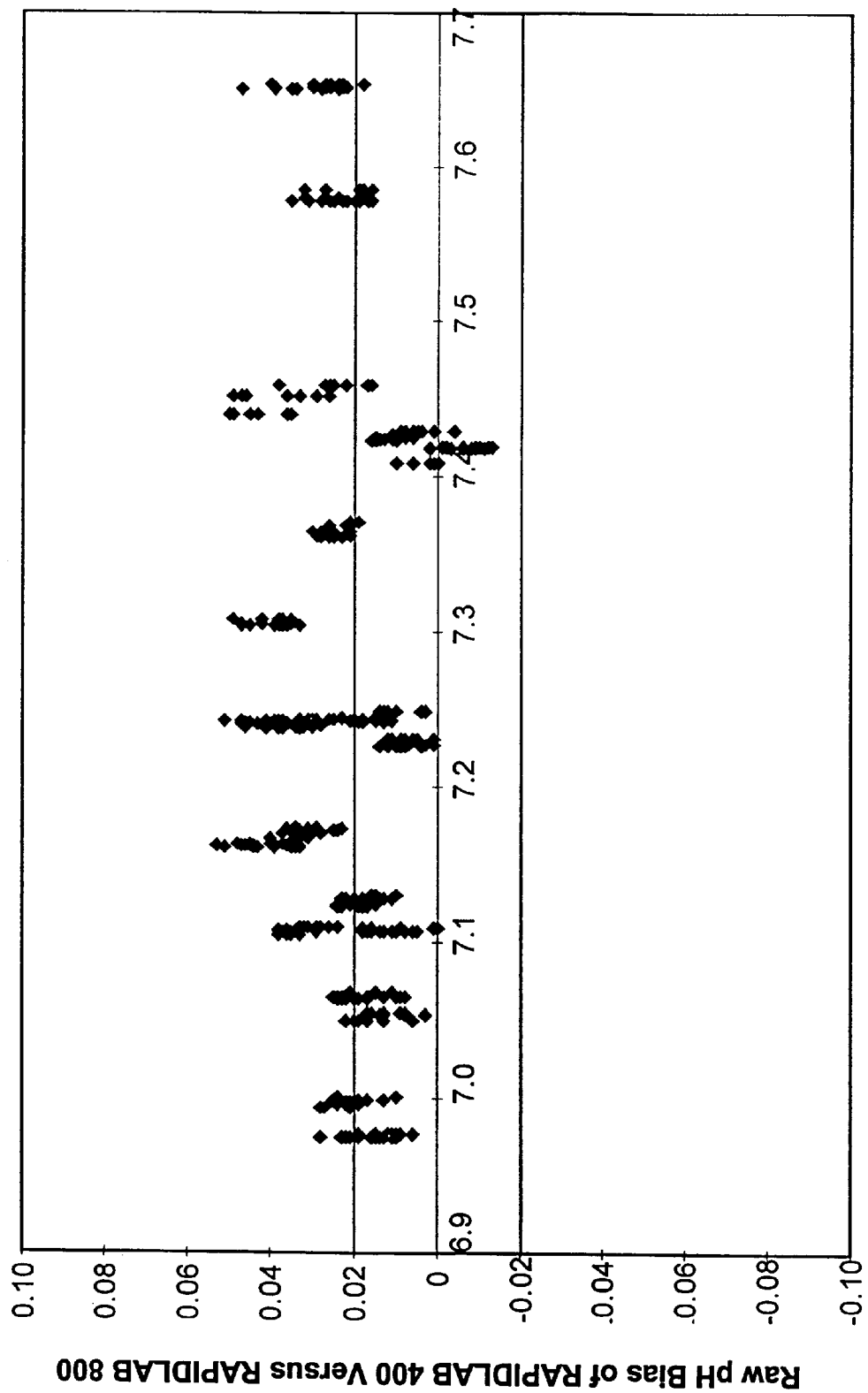
FIG. 1 is plot showing whole blood data showing pH bias obtained from an instrument having a polymeric membrane based planar pH electrode as referenced against pH values taken from an instrument having a glass pH sensor, as described in EXAMPLE 1.

It has been discovered that pH bias associated with membrane based pH sensors does not exist in samples that do not contain protein. It has also been discovered that protein induces an apparent bicarbonate ion concentration ([$HCO_3^-$]) interference. The pH bias has also been found to vary as a function of protein loading. Additionally, this protein-induced bias in membrane-based pH sensors was found to be relatively constant in the normal protein range (typically ranging from about 4 to about 8 g/dL) such that the total pH bias in this protein range is a function of [$HCO_3^-$]. Thus, in the normal protein range, the pH bias can be corrected for by a single equation using the available [$HCO_3^-$] value or the protein value itself. As provided by the correcting equation, the pH bias is reduced to provide clinically acceptable pH readings. To be clinically acceptable, preferably the pH readings have a pH bias of less than about ±0.04 pH units, more preferably less than about ±0.02 pH units, and most preferably the pH bias falls within a range from 0 to ±0.02 pH units.

The protein induced $HCO_3^-$ interference applies to all systems which use solvent polymeric membrane-based pH sensors, known in the art as an Ion Selective Electrodes (ISE) or other formats such as Ion Selective Field Effect Transistors and the like. According to the invention, the derived correction is second order in nature and may be modeled after the correcting equation shown in Equation [2*], as follows $$Y=a^*[HCO_3^-]^2+b^*[HCO_3^-]c \qquad [2^*]$$

Where Y is defined as the correction factor, a*, b* and c are empirically derived coefficients, as defined in Equation 1* herein, and [$HCO_3^-$] is the bicarbonate concentration of the patient sample as measured or calculated by a sensing instrument. As known to those skilled in the are, empirical implies that the coefficients are obtained by fitting the raw data to the equation.

Any patient sample may be tested using the inventive method. Non-liquid samples may be prepared as liquid samples and thereafter tested if desired, by techniques known to those skilled in the art. Whole blood may be directly tested using the method without requiring additional manipulation of the sample.

Components described herein, as well as additional features, may be arranged in the planar format on non-conductive substrates in various configurations. The membrane based pH electrode may be prepared in any number of suitable formats, such as, for example, those described in Clinical Chemistry 43, No. 9, 1997. Polymeric materials for the membrane based pH electrodes are described in Analytical Chemistry, 1986, 58, 2285–2289. As known to those skilled in the art, the bicarbonate value of the sample may be obtained either directly or indirectly. For example a direct measurement may be accomplished by using an ISE selective for $HCO_3^-$ on the sensing instrument. Alternatively, the $HCO_3^-$ value of a sample may be derived from measurement of partial pressure of carbon dioxide ($pCO_2$) or Total $CO_2$ and then calculated as known in the art or by measurement of $CO_3^{2-}$ and then calculated as known in the art.

As known to those skilled in the art, the sensing instrument for the ion selective electrodes may have any number of designs to enable a potential reading of the sample is obtained between the pH electrode and a suitable reference (such as for example, a silver/silver halide reference electrode).

According to the invention, because protein induces an interference in the pH readings obtained from polymeric based pH membrane electrodes, one skilled in the art may use a correction equation on the raw pH value to obtain a more accurate reading. While the measured protein level of the sample may be used directly in a correction equation, the use of the bicarbonate level is a preferred because bicarbonate is commonly measured or derived on the same sensing instrument that provides pH readings of patient samples. The correction of the raw pH data may occur on-line as incorporated within the software of the sensing instrument or off-line as corrected manually or within the software of a diagnostic system that incorporates a number of instruments testing the same patient sample.

The design of the circuitry of a sensing instrument that having ion selective electrodes that may utilize the invention is within the skill of those familiar with the technology. For example, the circuitry described in *Ion-Selective Electrode Methodology,* Vol. I, Ed. Arthur K. Covington, CRC Press, 1979, pp. 32–33. (hereby incorporated by reference) may be utilized.

EXAMPLES

Example 1

Data was collected from testing in excess of 200 whole blood samples using a planar-based instrument RAPIDPOINT 400, manufactured by Bayer Corporation, Medfield, Mass. The RAPIDPOINT 400 Sensing Instrument utilizes solvent polymeric based pH membrane electrodes having a planar format (prepared with materials described in *Analytical Chemistry,* 1986, 58, 2285–2289 and in the format described in *Clinical Chemistry* 43, No. 9, 1997) and planar membrane based bicarbonate electrodes (prepared as described in U.S. Pat. No. 5,554,272).

The data from RAPIDPOINT 400 were compared to standards provided by measuring the same patient samples for pH using three-dimensional glass based sensors in the RAPIDLAB 800 Sensing Instrument. The plotted data, as shown in FIG. 1, is the RAPIDPOINT 400 pH bias to RAPIDLAB 800 pH versus RAPIDLAB 800 pH values. As shown, the pH bias of the data from the RAPIDPOINT 400 extended to ±0.06 pH units.

Example 2

Figure 2:
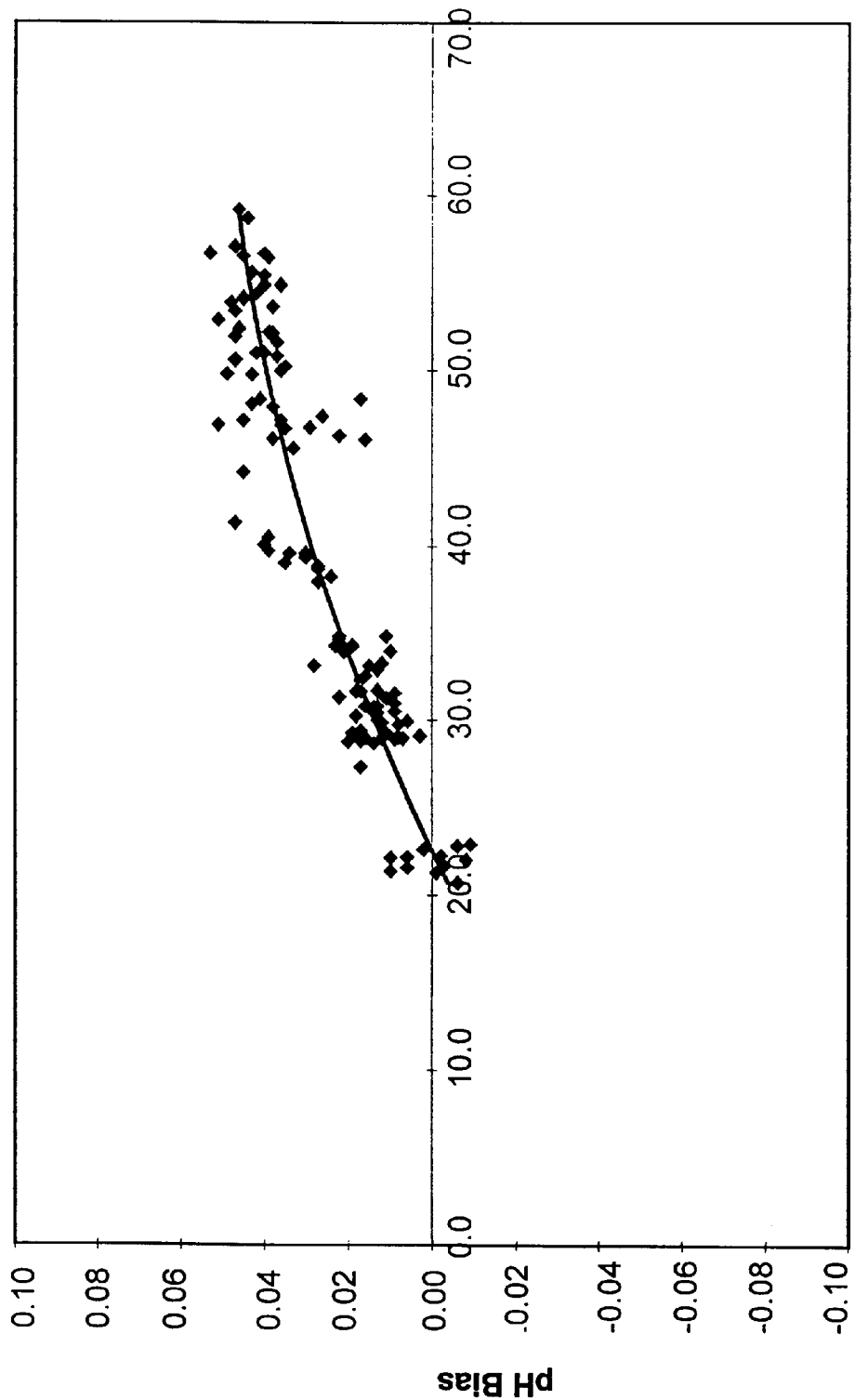
FIG. 2 a plot of data showing a direct correlation of pH bias to increasing [$HCO_3^-$] values of the samples, as described in EXAMPLE 2.

As shown in FIG. 2, a plot of data was prepared using the planar pH RAPIDPOINT 400 pH bias versus RAPIDPOINT 400 calculated [$HCO_3^-$] via the Henderson-Hasselbach equation. The data were derived from the plot shown in FIG. 1. As shown in FIG. 2, there is a direct correlation of pH bias to increasing [$HCO_3^-$] values of the samples.

Example 3

Figure 3:
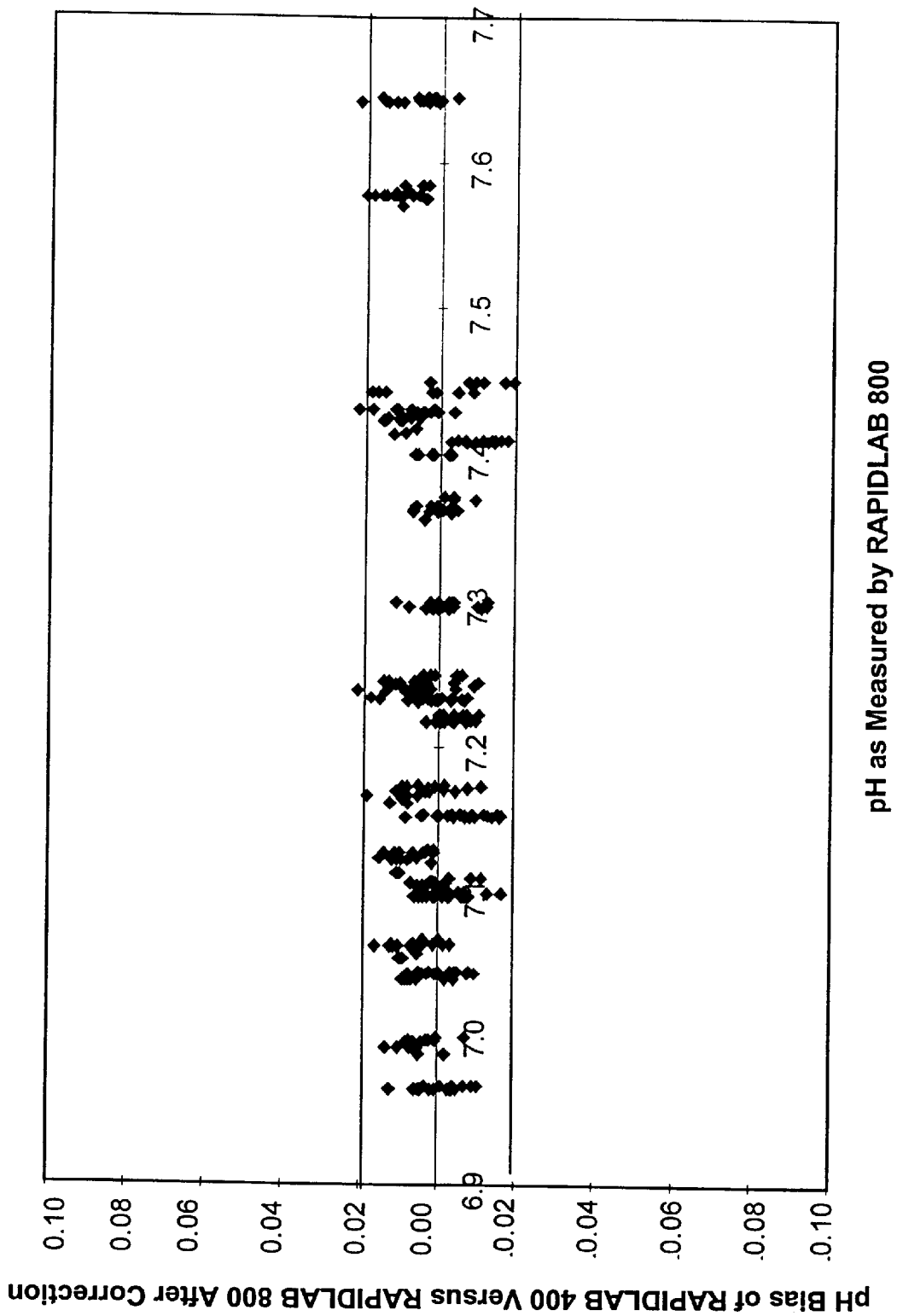
FIG. 3 is a plot showing pH data corrected by the invention as described in EXAMPLE 3.

A correction of the increasing $HCO_3^-$ values shown in EXAMPLE 2 was derived to correct the pH data of EXAMPLE 1. The derived correction was applied to the raw pH data from the RAPIDPOINT 400 utilizing Equation [1*] as described previously herein. By application of the correction equation, significant improvement in the pH sat from the planar pH electrodes of EXAMPLE 1 was observed, as shown by the corrected data of EXAMPLE 1 plotted in FIG. 3. As the data provided, the pH bias was reduced to ±0.02 pH units.

Other modifications of practicing the invention are possible. It would be possible to correct for both the protein level and the $[HCO_3^-]$ if the protein level of the samples was known. For example, one could use the measured $[HCO_3^-]$ using a bicarbonate electrode or use $HCO_3^-$ activities instead of using the calculated $[HCO_3^-]$ used in the present EXAMPLES, as is known in the art and shown in Analytical Chemistry, 1982, 54, 423–429. One could have any form of the correcting equation that is desired as long as it corrects for the apparent $[HCO_3^-]$. For example it could be linear, quadratic, $n^{th}$-order polynomial, spline, empirically derived or a combination thereof. As known to those skilled in the art, $[HCO_3^-]$ represents bicarbonate concentration whereas $HCO_3^-$ represents bicarbonate ion.

Various modifications to the invention will be apparent to and can readily be made by those skilled in the art, given the disclosure herein, without departing from the scope and materials of this invention. It is not, however, intended that the scope of the claims appended hereto be limited to the description as set forth herein, but rather that the claims be construed as encompassing all features of patentable novelty which reside in the present invention, including all features which would be treated as equivalents thereof by those skilled in the art to which the invention pertains. It is also noted that the examples given herein are intended to illustrate and not to limit the invention.

That which is claimed is:

1. A method of measuring pH with a sensing instrument that employs an ion-selective polymeric-membrane-based pH electrode, the method comprising:
   using said electrode to obtain a raw pH measurement of a protein-containing liquid sample;
   determining the bicarbonate concentration of said protein-containing liquid sample; and
   correcting said raw pH measurement for interference induced by the presence of protein in said protein-containing liquid samples to calculate a corrected pH value by using a correction factor and the raw pH measurement, wherein the correction factor is a function of the bicarbonate concentration of the sample.

2. The method according to claim 1, wherein the corrected pH value is within about ±0.04 pH units from a pH measurement that would be obtained for the protein-containing liquid sample using a glass-based pH sensor.

3. The method according to claim 1, wherein the corrected pH value is within about ±0.02 pH units from a pH measurement that would be obtained for the protein-containing liquid sample using a glass-based pH sensor.

4. The method according to claim 3, wherein the correcting step comprises subtracting the correction factor from the raw pH measurement.

5. The method according to claim 4, wherein the protein-containing liquid sample exhibits a protein concentration of about 4 to about 8 g/dL.

6. The method according to claim 5, wherein the correction factor is defined by the equation $\{Y=a^*[HCO_3^-]^2+b^*[HCO_3^-]-c\}$, where Y is the correction factor, $a^*$, $b^*$ and c are empirically derived coefficients and $[HCO_3^-]$ is the bicarbonate concentration of said sample.

7. The method according to claim 6, wherein said bicarbonate concentration is determined with an electrode specific to bicarbonate.

8. A method of reducing error in measuring pH using a planar polymeric-membrane-based pH electrode, said method comprising:
   (a) measuring the pH of a protein-containing liquid sample using said planar polymeric-membrane-based electrode to obtain a raw pH measurement;
   (b) determining the bicarbonate concentration of said protein-containing liquid sample;
   (c) calculating a corrected pH value by subtracting from the raw pH measurement a correction factor defined by the equation $\{Y=a^*[HCO_3^-]^2+b^*[HCO_3^-]-c\}$, where Y is the correction factor, $a^*$, $b^*$, and c are empirically derived coefficients and $[HCO_3^-]$ is the bicarbonate concentration of said sample.

9. The method according to claim 8, wherein said bicarbonate concentration is derived from a measurement of partial pressure of carbon dioxide.

10. The method according to claim 8, wherein said bicarbonate concentration is derived from a measurement of total $CO_2$.

11. The method according to claim 8, wherein said bicarbonate concentration is derived from a measurement of total $CO_3^{2-}$.

12. The method according to claim 8, wherein said bicarbonate concentration is determined by using an ion-selective electrode specific for $HCO_3^-$.

13. A method of measuring pH, said method comprising:
   (a) contacting a protein-containing liquid sample with an ion-selective polymeric-membrane-based pH electrode, a second electrode and a reference electrode, each electrode connected to a sensing instrument;
   (b) providing an electrical current between the ion-selective polymeric-membrane-based pH electrode and the reference electrode to allow the sensing instrument to derive a raw pH measurement;
   (c) using the second electrode to provide the sensing instrument the bicarbonate concentration for the protein-containing liquid sample;
   (d) allowing the sensing instrument to calculate a corrected pH value by subtracting from the raw pH measurement a correction factor defined by the equation $\{Y=a^*[HCO_3^-]^2+b^*[HCO_3^-]-c\}$, where Y is the correction factor, $a^*$, $b^*$ and c are empirically derived coefficients and $[HCO_3^-]$ is the bicarbonate concentration of said sample.

14. The method according to claim 13, wherein the corrected pH value is within about ±0.04 pH units from a pH measurement that would be obtained for the protein-containing liquid sample using a glass-based pH sensor.

15. The method according to claim 14, wherein the corrected pH value is within about ±0.02 pH units from a pH measurement that would be obtained for the protein-containing liquid sample using a glass-based pH sensor.

16. The method according to claim 15, wherein the protein-containing liquid sample exhibits a protein concentration of about 4 to about 8 g/dL.

17. A method of correcting for the presence of protein in a liquid sample when using a system to measure the pH of the liquid samples, the system comprising a software-driven sensing instrument and an ion-selective polymeric-membrane-based pH electrode operatively connected to the sensing instrument, said method comprising using said electrode to obtain a raw pH measurement of the liquid sample;

providing the bicarbonate concentration of said protein-containing liquid sample; and allowing software of the sensing instrument to use a correcting equation, the raw pH measurement and the bicarbonate concentration to calculate a corrected pH value that accounts for the presence of protein in the liquid sample.

18. The method according to claim 17, wherein the bicarbonate concentration is determined by obtaining 200 raw pH measurements using said electrode and comparing the raw pH measurements with corresponding pH measurements using a glass-based pH sensor.

19. The method of claim 18, wherein the corrected pH value is within about ±0.04 pH units from a pH measurement that would be obtained for the protein-containing liquid sample using the glass-based pH sensor.

20. The method according to claim 18, wherein the corrected pH value is within about ±0.02 pH units from a pH measurement that would be obtained for the protein-containing liquid sample using the glass-based pH sensor.

* * * * *